United States Patent [19]

Mauz

[11] Patent Number: 4,839,439
[45] Date of Patent: Jun. 13, 1989

[54] PREPARATION OF POLYMER BASED ON POLYVINYLENE CARBONATE AND/OR POLYHYDROXYMETHYLENE

[75] Inventor: Otto Mauz, Liederbach, Fed. Rep. of Germany

[73] Assignee: Hoechst Aktiengesellcshaft, Frankfurt am Main, Fed. Rep. of Germany

[21] Appl. No.: 207,788

[22] Filed: Jun. 17, 1988

Related U.S. Application Data

[60] Division of Ser. No. 1,918, Jan. 9, 1987, Pat. No. 4,788,278, which is a continuation of Ser. No. 721,913, Apr. 11, 1985, abandoned.

[30] Foreign Application Priority Data

Apr. 13, 1984 [DE] Fed. Rep. of Germany ....... 3413904

[51] Int. Cl.$^4$ ............................................. C08F 34/02
[52] U.S. Cl. .................................... 526/203; 524/457; 524/460; 524/549; 526/209; 526/210; 526/213; 526/220; 526/269; 528/370; 528/371
[58] Field of Search ............... 526/203, 209, 210, 213, 526/220, 269; 524/457, 460, 549; 528/370, 371

[56] References Cited

U.S. PATENT DOCUMENTS 4,788,278 11/1988 Mauz ................................. 528/370

*Primary Examiner*—Harold D. Anderson
*Attorney, Agent, or Firm*—Finnegan, Henderson, Farabow, Garrett, & Dunner

[57] ABSTRACT

The invention relates to modified polymers based on polyvinylene carbonate and/or polyhydroxymethylene, the modification being effected by particular alkoxylated compounds incorporated into the polymer. These polymers, for the preparation of which, according to the invention, particular dispersion stabilizers are used, are suitable, inter alia, as carriers for biologically active substances or for affinity chromatography.

7 Claims, No Drawings

PREPARATION OF POLYMER BASED ON POLYVINYLENE CARBONATE AND/OR POLYHYDROXYMETHYLENE

This is a division of application Ser. No. 001,918, filed Jan. 9, 1987 now U.S. Pat. No. 4,788,278, which was a continuation of application Ser. No. 721,913, filed Apr. 11, 1985, now abandoned.

The preparation of high molecular weight polyvinylene carbonate by free radical-initiated polymerization of the monomer in bulk or in solution is known (cf. J. Polymer Sci. 58 (1962), pages 533 et seq.). The same also applies to the copolymerization of vinylene carbonate with various vinyl compounds (cf. U.S. Pat. Nos. 2,722,525; 2,847,398; 2,847,401; 2,847,402; 2,934,514; 2,945,836 and 2,957,847). Vinylene carbonate polymers have are used as plastics material, as binders and as impregnating agents (cf. U.S. Pat. Nos. 2,794,013 and 2,930,779).

It is also known that polyvinylene carbonate can be converted into poyhydroxymethylene by acid or alkaline hydrolysis.

Processing of polyvinylene carbonate and its hydrolysis product polyhydroxymethylene to films, fibers and sheets is known from German Offenlegungsschrift No. 1,494,576.

A process for the preparation of polymers and copolymers of vinylene carbonate, in which the polymerization is carried out in the presence of an organic dispersant and nonionic, surface-active organic compounds are added as dispersion stabilizers is known from German Offenlegungsschrift No. 2,556,759. Oxyethylated saturated fatty alcohols are also mentioned, inter alia, as dispersion stabilizers. However, in carrying out this process, agglomeration of the polymer particles occurs as the polymerization advances. Such a product is not very suitable for further processing.

The object of the present invention was therefore to provide a modified polyvinylene carbonate which is easy to prepare or a modified polyhydroxymethylene of adjustable hydrophilicity, in which the hydrophilicity essentially should not be adjusted by incorporation of comonomers or by modification of the cyclocarbonate groups.

To achieve this object, the invention proposes a polymer which essentially consists of the units

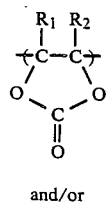

and/or

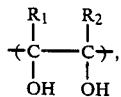

in which $R_1$ and/or $R_2$ denote hydrogen or a monovalent hydrocarbon radical with up to 8 carbon atoms, and, if appropriate, small amounts of other monomer units, which also contains covalently bonded units which are derived from at least one compound of the formula

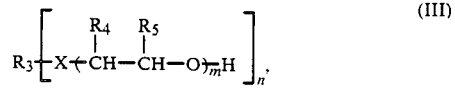

in which:

$R_3$ denotes a hydrocarbon radical with 4 to 30 carbon atoms, preferably an alkyl radical with 4 to 30 carbon atoms, preferably 12 to 20 carbon atoms, or an aryl radical with 6 to 14 carbon atoms, preferably 6 to 10 carbon atoms, preferably a phenyl radical, it being possible for this aryl (phenyl) radical optionally to be substituted by at least one, preferably 1 to 3, alkyl radicals with 4 to 30 carbon atoms, preferably 12 to 20 carbon atoms;

X denotes —O—, —NH— and/or —COO—, preferably —COO— and/or —O—;

$R_4$ and $R_5$ denote hydrogen or a monovalent hydrocarbon radical, in particular an alkyl radical, with 1 to 8 carbon atoms, with the proviso that at least one of the radicals $R_4$ or $R_5$ is hydrogen;

m denotes an integer from 1 to 40, preferably 5 to 35; and n denotes an integer from 1 to 4, preferably 1 to 2.

The invention furthermore relates to a process for the preparation of such polymers by polymerization of compounds of the formula

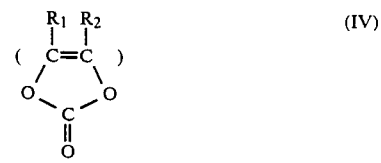

in which $R_1$ and $R_2$ have the above meaning, and, if appropriate, small amounts of other monomers copolymerizable with these compounds, the polymerization being carried out in a liquid dispersant in the presence of a free radical initiator and a dispersion stabilizer, and, if appropriate, hydrolysis of the cyclocarbonate rings of the resulting product, which comprises carrying out the polymerization in the presence of at least one compound of the formula (III) and using, as the disperson stabilizer, a copolymer of maleic anhydride and a vinyl alkyl ether and/or a vinyl ester and/or a longer-chain α-olefin.

Finally, the invention also relates to the use of the resulting polymers, if appropriate after reaction with spacers, as carriers for the preparation of carrier-bound biologically active substances, as adsorbents in affinity chromatography or gel chromatography or for the production of shaped articles.

The base polymer of the polymer according to the invention essentially preferably consists of at least 90% by weight of the above units (I) and/or (II) in which $R_1$ and/or $R_2$ denote hydrogen or a monovalent hydrocarbon radical with up to 8 carbon atoms, preferably an alkyl radical with 1 to 6 carbon atoms and in particular an alkyl radical with 1 to 4 carbon atoms. Examples of these are: the methyl, ethyl, isopropyl, 2-ethylhexyl, n-heptyl, cyclopentyl, phenyl, totyl, benzyl and xylyl radicals.

The radicals $R_1$ and $R_2$ preferably represent hydrogen.

According to another preferred embodiment of the invention, the amount of units (II) is more that 50% by weight, based on the total amount of (I) and (II), i.e. the majority of the cyclocarbonate groups of (I) have been hydrolyzed to hydroxyl groups. In particular, the amount of (II) is at least 95% by weight and particularly preferably 100% by weight.

If appropriate, the base polymer can also contain small amounts of other monomer units derived from monomers which are copolymerizable with vinylene carbonate or derivatives thereof. These monomers can also contain hydrophilic or crosslinking groups. Examples of such monomers which may be mentioned here are: vinylpyrrolidone, alkyl(meth)acrylates with in each case 2 to 6 carbon atoms in the alkyl group, hydroxyalkyl esters of (meth)acrylic acid with 2 to 6 carbon atoms in the alkyl group, N-vinyl-N-alkylacetamide ($C_1$-$C_4$-alkyl), vinyl acetate, divinyl ethers of glycols, such as ethylene glycol divinyl ether, butanedioldivinyl ether and hexanedioldivinyl ether, N,N'-alkylenebis(meth)acrylamides with straight-chain or branched alkylene radicals containing up to 12 carbon atoms, preferably up to 6 carbon atoms, such as N,N'-methylenebisacrylamide, N,N'-ethylenebisarcylamide, N,N'-hexamethylenebisacrylamide, N,N'-methylenebismethacrylamide, N,N'-ethylenebismethacrylamide, N,N'-hexamethylenebismethacrylamide, N,N'-ethylenebisacrylamide, glyoxalbisacrylamide, (1,2-bisacrylamido-1,2-dihydroxyethane), bisacrylamidoacetic acid, ethylene glycol bis-methacrylic acid glycol bis-methacrylic acid ester, butanediol bismethacrylic acid ester, triallyl cyanurate, trisacryloylperhydrotriazine, dibinylbenzene, divinyl adipate, N,N'-divinylethyleneurea, N,N'-divinylpropyleneurea, ethylidene-bis-3-(N-vinylpyrrolidone), N,N'-divinyldiimidazol-2,2'-yl- and 1,1'-bis(3,3'-vinylbenzimidazolid-2-one)-1,4-butane, vinyl acrylate, allyl methacrylate, acrylic and methacrylic acid esters with 5–12 carbon atoms in the alkyl radical, (meth)acrylonitrile, vinyl esters with 4–18 carbon atoms in the carboxylic acid radical, such as vinyl butyrate and vinyl stearate, and vinyl esters of the branched carboxylic acids with 10 to 12 carbon atoms; and furthermore vinylaromatics, such as styrene or α-methylstyrene.

The base polymer can also contain several units derived from these monomers.

The amount of these monomer units—if present—in general does not exceed 15% by weight and is preferably not more than 10% by weight, in each case based on the total base polymer. Crosslinking monomer units, for example in amounts of 0.2–5 mol %, preferably 0.5–3 mol %, lead to a higher mechanical stability, which may be advantageous for use in column chromatography.

However, the base polymer preferably consists only of units (I) and/or (II).

As the innovation according to the invention, the base polymer contains units which are derived from at least one comound of the formula (III). These units can also originate from different compounds of the formula (III), i.e. mixtures of the various compounds of the formula (III) can also be used in the preparation of the polymers according to the invention.

The amount of these units of the formula (III) is as a rule up to 30% by weight, preferably 1 to 20% by weight and in particular 7 to 15% by weight, in each case based on the base polymer.

In the above formula (III), the individual substituents preferably are as follows:

$R_3$ denotes a branched or, preferably, straight-chain alkyl radical with 4 to 30 carbon atoms, preferably 12 to 20 carbon atoms. Examples which may be mentioned are: hexyl, heptyl, octyl, nonyl, decyl, undecyl, dodecyl, hexadecyl, octadecyl and eicosyl;

X denotes —O—; or —COO—; in particular —O—;

$R_4$ and $R_5$ denote hydrogen or methyl, in particular hydrogen;

m denotes an integer from 5 to 35; and n denotes 1 or 2, in particular 1.

Preferred representatives of the formula (III) are accordingly oxethylated, monobasic, aliphatic carboxylic acids (alkyl ($C_{4-30}$)), mixtures of such acids (for example fatty acids) also being possible. Particularly preferred representatives which may be mentioned here are oxyethylated monohydric aliphatic alcohols (alkyl ($C_{4-30}$)), which are preferably primary. Mixtures of such alcohols (for example fatty alcohols) can also be used here.

Representatives of the formula (III) which are less preferred are, for example, corresponding oxyethylated, monofunctional amines, in particular primary amines (where X=—NH—), oxyethylated hydroxycarboxylic acids (where X=—O— or —COO—; and n=2), oxyethylated aromatic carboxylic acids ($R_3$=a phenyl radical) or polyhydric/polybasic alcohols/carboxylic acids (n>1).

From the above statements, preferred polymers according to the invention are accordingly polyvinylene carbonate and/or polyhydroxymethylene in each case containing units of oxyethylated monobasic aliphatic carboxylic acids (alkyl ($C_{4-30}$)), or, in particular, oxyethylated monohydric aliphatic alcohols (alkyl ($C_{4-30}$)) preferably in amounts of 1 to 20% by weight and in particular 7 to 15% by weight.

According to the invention, the base polymer and the units of the compounds of the formula (III) are linked to one another by covalent bonds. Without being specific, the majority of the units of the formula (III) incorporated in the polymer according to the invention are probably grafted onto the base polymer. In addition, incorporation as end groups is also conceivable. At higher numerical values of m, i.e. with longer polyether radicals, grafting of polyvinylene carbonate chains on to the alkoxylated compounds of the formula (III) is also possible.

The process according to the invention for the preparation of the claimed polymers is preferably carried out under the usual known conditions of bead polymerization, such as are described, for example, in German Offenlegungsschrift No. 2,237,316, or German Offenlegungsschrift No. 2,556,759, but with the innovation that particular dispersion stabilizers are used.

These are preferably alternating copolymers of maleic anhydride and a vinyl alkyl ether, preferably a vinyl n-alkyl ether with 6 to 30 carbon atoms, preferably 10 to 20 carbon atoms, in the alkyl group, or a vinyl ester with 6 to 30 carbon atoms, preferably 10 to 20 carbon atoms, in the carboxylic acid group, or a longer-chain α-olefin with 8 to 30 carbon atoms, preferably 10 to 20 carbon atoms. Examples which may be mentioned here of such vinyl alkyl ethers, vinyl esters and longer-chain α-olefins are: vinyl octyl ether, vinyl decyl ether, vinyl dodecyl ether, vinyl stearyl ether, vinyl myricyl ether, vinyl ethylhexanoate, vinyl isononanoate, vinyl versitate, vinyl laurate, vinyl stearate and vinyl esters of branched carboxylic acids with 10 to 12 carbon atoms;

and oct-1-ene, dec-1-ene, tetradec-1-ene, octadec-1-ene and tricos-1-ene.

These dispersion stabilizers, which can also be used as a mixture, are even effective in amounts of 0.001% by weight, based on the total amount of monomers. Amounts of 0.005 to 10% by weight, preferably 0.01–5% by weight, based on the total amount of monomers, are usually employed.

The reduced specific viscosity (RSV) of these copolymers employed as dispersion stabilizers is as a rule between 0.01 and 0.1 dl/g (determined in 0.6% strength solution in toluene at 25° C.). The corresponding preferred range is 0.05 to 1.0 dl/g for the copolymers of maleic anhydride and vinyl alkyl ethers or vinyl esters and 0.01 to 0.1 dl/g for the copolymers of maleic anhydride and a longer-chain α-olefin. The molar ratio of maleic anhydride to vinyl alkyl ether or vinyl ester or to longer-chain α-olefin is generally between 1:4 and 1:1, preferably between 1:2 and 1:1 and in particular 1:1.

According to the invention, possible free radical initiators are those which are readily soluble in the monomer phase and have the minimum possible solubility in the liquid dispersant. Examples of these are organic peroxides, such as di-tert.-butyl peroxide, dibenzoyl peroxide, bis(o-methylbenzoyl) peroxide, tert.-butyl hydroperoxide, cumene hydroperoxide, di-isopropyl peroxydicarbonate and cyclohexanone peroxide, or aliphatic azo compounds, such as α,α'-azodiisobutyronitrile, azobiscyanovaleric acid, 1,1'-azocyclohexane-1,1'-dicarboxylic acid nitrile and azodicarboxamide. If appropriate, the corresponding redox systems can also be used. The amount of initiator is usually 0.01 to 5% by weight, preferably 0.1 to 2% by weight (based on the total amount of the monomers).

The liquid dispersants used to carry out the bead polymerization according to the invention are, in particular, those organic compounds which are liquid under normal conditions and have a boiling point above 60° C., preferably in the range from 85° to 300° C., and in which, preferably, the monomers, the polymer and preferably also the initiator are insoluble, or at any rate dissolve only in traces, under the polymerization conditions. Hydrocarbons with 6 to 20, preferably 8 to 16, carbon atoms, in particular paraffins, for example, are particularly suitable. A mixture of various compounds can also be employed as the dispersant. Examples of suitable hydrocarbons or hydrocarbon mixtures are n-hexane, n-heptane, n-octane, cyclohexane, iso-octane, benzine fractions with boiling ranges between 90° and 170° C. and light liquid paraffin (Deutsches Arzneibuch (German Pharmacopeia), 7th edition, DAB 7). The ratio of the monomer phase to the dispersant phase can vary within wide limits, for example 1:1 and 1:50, preferably 0.5:1 and 1:15 (weight ratio).

According to the invention, the polymerization of the monomers of the formula (IV) and, if appropriate, other monomers copolymerizable with these monomers is carried out in the presence of the compounds of the formula (III), preferably an oxyethylated alcohol and/or an oxyethylated carboxylic acid, these compounds being incorporated into the resulting base polymer, and certainly predominantly by grafting.

The preparation of the compounds of the formula (III) is known and is effected by adding 1 to 40, preferably 5 to 35, moles of alkylene oxide, preferably ethylene oxide, onto one mole of the corresponding starting compound $$R_3[XH]_n \quad (V)$$

in which $R_3$, $X$ and $n$ have the meaning given for formula (III), i.e. for example, onto alcohols, amines, carboxylic acids, hydroxycarboxylic acids and the like. The upper limit of 40 moles is not critical here, but substantially larger amounts of alkylene oxide provide no advantages.

Examples of representatives of the formula (V) are: monofunctional aliphatic alcohols (amines), such as hexyl, ethylhexyl, heptyl, octyl, nonyl, decyl, undecyl, dodecyl, hexadecyl, octadecyl, eicosyl alcohol (and the corresponding amines); monofunctional phenols (aromatic amines), such as hexylphenol (hexylphenylamine), nonylphenol (nonylphenylamine) and dodecylphenol (dodecylphenylamine); and monobasic aliphatic carboxylic acids, such as pentanoic acid, hexanoic acid, octanoic acid, decanoic acid, undecanoic acid, dedecanoic acid, tetradecanoic acid, hexadecanoic acid, heptadecanoic acid, octadecanoic acid, eicosanoic acid, versatic acid, montanic acid and the like.

The compounds of the formula (III) are employed in an amount such that the abovementioned incorporated amounts result in the polymer. In general, these amounts of the compounds (III), which, furthermore, are easy to determine experimentally, are up to 30% by weight, preferably 1 to 20% by weight and in particular 7 to 15% by weight, based on the monomer (IV) or the monomer mixture.

The process according to the invention is advantageously carried out in a reaction vessel provided with a stirring device, usually at temperatures of 20° to 150° C., preferably 60° to 130° C. The particle size of the polymer obtained is adjusted in a known manner by means of the stirring speed and the phase ratio. It is particularly advanageous to use a vertical, cylindrical vessel which has a flat bottom and is provided with a coaxially arranged stirrer, the shaft of which extends almost to the bottom of the vessel. The reaction vessel is preferably vacuum-resistant and can be equipped with a reflux condenser, feed funnel, gas inlet tube and temperature-measuring apparatus. The vessel is in general heated and cooled by means of a liquid bath, for example an oil bath or water bath. It is advantageous to carry out the process according to the invention in the absence of atmospheric oxygen. The reaction vessel is therefore flushed with an inert gas, preferably nitrogen, before the start of the reaction.

When the polymerization reaction has ended, the unreacted monomer is removed from the reaction vessel, for example by evaporation under reduced pressure, preferably under a pressure of 0.1–15 mm Hg, or by decantation, filtration or filtration with suction of the supernatant liquor. If necessary, the polymer is then washed with low-boiling organic solvents, for example a hydrocarbon, a lower alcohol or acetone, and is finally dried. The polymer is usually dried at a temperature of 20° to 100° C., preferably 40°–80° C.; drying under reduced pressure is recommended.

If the reaction has been carried out under the conditions of bead polymerization, the polymer obtainable by the process according to the invention consists—before the hydrolysis which is preferably carried out—of predominantly spherical particles (beads), the average particle size of which in the dry, non-swollen state is 20 to 800 μm, preferably 50 to 300 μm, and which preferably have a narrow particle size distribution. The particular optimum particle size chiefly depends on the specific field of use.

As mentioned, the polymer obtained immediately after the process according to the invention is preferably subjected to hydrolysis, during which the cyclic carbonate groups are opened and are converted into hydroxyl groups, carbon dioxide being split off. The acid or alkaline hydrolysis can be carried out under the known conditions, such as are described, for example, in J. Polym. Sci. 31, 237 (1958).

The products obtainable according to the invention are suitable, for example, as carriers for biologically active substances, as adsorbents (affinity resins), for example, for blood filtration or in gel chromatography, and for shaped articles (films, fibers and the like) as diagnostics in laboratory medicine (test strips) and the like.

If the product is used as a carrier for biologically active substances, this is first reacted, if appropriate, with so-called spacers. According to the invention, possible spacers are the homo- and hetero-bifunctional compounds known for this purpose, in which the second functional group takes over the coupling with the biologically active substance to be fixed (cf. German Pat. Nos. 2,421,789 and 2,552,510, as well as Ullmanns Encyclopädie der technischen Chemie (Ullmann's Encyclopedia of Industrial Chemistry), 4th edition, volume 10, page 540 and "Characterization of Immobilized Biocatalysts", Verlag Chemie, Weinheim, 1979, page 53).

The term "biologically active substances" is to be understood as meaning the known naturally occurring or synthetically prepared substances which are active in vivo or in vitro, such as enzymes, activators, inhibitors, antigens, antibodies, vitamins, hormones, effectors, antibiotics, proteins and the like. The latter term here also includes proteins with certain non-protein substituents, such as metal ions, polysaccharides, porphyrin groups, adenine dinucleotide, ribonucleic acid, phospholipids and the like. Polypeptide fragments, for example the active parts of enzyme molecules, also fall within the term biologically active substances.

The invention is illustrated in more detail below with the aid of examples.

EXAMPLE 1

(a) 200 g of isooctane, 3.5 g of oxyethylated stearyl alcohol with 25 ethylene oxide units and 0.75 g of a 1:1 copolymer of maleic anhydride and octadec-1-ene (RSV value: 0.064 [dl/g] in 0.6% strength solution in toluene at 26° C.) were initially introduced into a cylindrical vessel with a cross-blade stirrer, reflux condenser, thermometer and nitrogen inlet tube. After the vessel had been flushed out with nitrogen and the mixture had been blanketed with nitrogen, 1 g of azodiisobutyronitrile, dissolved in 150 g (=110 ml) of vinylene carbonate, was added at a stirrer speed of 250 rpm. Vigorous evolution of heat started at about 80° C. The temperature rose rapidly within minutes, so that vigorous reflux occurred. When the main reaction had ended, the mixture was afterpolymerized at 95° C. for about a further 3 hours. When the reaction had ended, the resulting polymer was filtered off with suction and washed several times with hexane. After drying in a vacuum cabinet at 50° C., 120 g (=80% of theory) of polyvinylene carbonate graft polynmer were obtained. It contained 2.0% by weight of ethoxy groups.

Analytical detection of the grafted-on oxyethylated alcohols or acids was carried out by determination of the oxyethyl group ($-C_2H_4O-$). The procedure for this analytical method is described in the journal "Industrial and Engineering Chemistry, volume 18, No. 8, August 1946, pages 500–504, Analytical Edition".

(b) 20 g of the polyvinylene carbonate graft polymer obtained above were stirred into 300 ml of 5N sodium hydroxide solution and hydrolyzed at 95° C. for 30 minutes. The product thereby dissolved. 2 l of water were now added and the mixture was neutralized with hydrochloric acid. The precipitated product was filtered off over a suction filter. After drying, 10 g of pulverulent material were obtained.

COMPARISON EXPERIMENT 1

Experiment 1 was repeated under the same experimental conditions, but without the disperser (copolymer of maleic anhydride/octadec-1-ene).

When the polymerization started, stirring had to be interrupted as a result of increasing agglutination of the polymer particles. At the end of polymerization lasting 3 hours without stirring, the reaction flask was shattered and the polymer was comminuted in a mill. The subsequent purification operation was carried out as described in Example 1. No oxyethyl radicals were found on analytical testing.

COMPARISON EXPERIMENT 2

(a) 1.5 g of a copolymer of maleic anhydride and octadec-1-ene were initially introduced into 970 g of isooctane in the experimental arrangement according to Example 1. 3 g of azodiisobutyronitrile were now dissolved in 450 g of vinylene carbonate and the solution was added to the above mixture. The bath temperature was slowly increased to 80° C. As the polymerization started, the internal temperature rose rapidly to 105°–110° (reflux). After-polymerization was carried out at 95° for 3 hours. No agglomeration of the polymer occurred, since the dispersion stabilizer according to the invention was present. After working up of the polymer, 380 g of polyvinylene carbonate were obtained.

(b) 40 g of the polyvinylene carbonate obtained as above were stirred in a mixture of 200 ml of methanol and 100 ml of 2 N sodium hydroxide solution at the reflux temperature for 3 hours. The sodium hydroxide solution was neutralized with dilute hydrochloric acid and the mixture was rinsed several times with water and then with acetone. After drying, 24 g of polyhydroxymethylene were obtained.

EXAMPLES 2–4

(a) The amounts of isooctane, oxyethylated stearyl alcohol and 1:1 copolymer of maleic anhydride and octadec-1-ene listed in Table 1 were mixed in the experimental arrangement described in Example 1. Azodiisobutyronitrile was then dissolved in vinylene carbonate and this solution was added. The polymerization and the working up were carried out in the manner described in Example 1.

(b) 20 g of the graft polyvinylene carbonate obtained according to Example 3 were hydrolyzed in a solution of 100 ml of methanol and 50 ml of 2N sodium hydroxide solution at the reflux temperature for 3 hours, with stirring. The sodium hydroxide solution was then neutralized with acetic acid. The precipitate was filtered off with suction, washed several times with water and then treated with acetone. After drying, 16 g of product were obtained.

TABLE 1

| | Amount of dispersant (g) | Amount of vinylene carbonate (g) | Oxyethylated stearyl alcohol with 25 ethylene oxide units (g) | Dispersion stabilizer (g) | Azodiiso-butyro-nitrile (g) | Incorporation of ethoxy groups (theory, % by weight) | Ethoxy groups (% by weight found) (degree of incorporation in %) | Yield | |
|---|---|---|---|---|---|---|---|---|---|
| Examples | | | | | | | | | |
| 1 | 200 | 150 | 3.5 | 0.75 | 1 | 2.3 | 2.2 [87] | 121 g | 76.5% |
| 2 | 200 | 150 | 9.0 | 1.0 | 1 | 5.6 | 5.5 [95] | 117 g | 76.1% |
| 3 | 200 | 150 | 30 | 0.3 | 1 | 16.6 | 20 [96] | 112 g | 62.2% |
| 4 | 970 | 450 | 45 | 1.0 | 3 | 9.1 | 7.8 [91] | 406 | 82% |
| Comparison experiment 1 | 200 | 150 | 3.5 | 0 | 1 | — | 0 | | |
| Comparison experiment 2 | 970 | 450 | 0 | 1.5 | 3 | — | — | 380 g | 84% |

EXAMPLE 5

200 g of isooctane, 6 g of oxyethylated octanol ($C_8H_{17}$—O—($CH_2$—$CH_2$—O)$_{10}$—H), 1 g of a 1:1 copolymer of maleic anhydride and vinyl octadecyl ether (RSV value=0.22 [dl/g] in 0.6% strength solution in toluene at 26° C.) were taken according to Example 1. 1 g of azodiisobutyronitrile in 150 g of vinylene carbonate was then added. The polymerization started at 70°–80°. The total polymerizaton time was about 3 hours. The polymer was filtered off with suction and washed several times with hexane and methanol. After drying, 115 g of product were obtained.

EXAMPLE 6

200 g of isooctane, 45 g of oxyethylated tallow fatty alcohol with 25 ethylene oxide units and 1.5 g of a 1:1 copolymer of maleic anhydride and octadec-1-ene (RSV value: 0.064 [dl/g] in 0.6% strength solution in toluene at 26° C.) were taken according to Example 1. 1 g of azodiisobutyronitrile in 150 g of vinylene carbonate was then added. The polymerization time was 3 hours at 95° C. After filtration with suction and washing out with hexane and methanol, 150 g of polymer were obtained, after drying (=77% yield).

EXAMPLE 7

300 ml of light liquid paraffin, 15 g of oxyethylated tallow fatty alcohol with 25 ethylene oxide units and 1.5 g of a 1:1 copolymer of maleic anhydride and octadec-1-ene (RSV value: 0.064 [dl/g] in 0.6% strength toluene solution at 26° C.) were taken according to Example 1. 1.5 g of azodiisobutyronitrile and 3 g of divinyleneurea, dissolved in 150 g of vinylene carbonate, were then added and the mixture was slowly heated up, with stirring. The temperature was maintained for 1 hour at 80° C. and then increased to 95° C. and polymerization was carried out for 5 hours.

The bead-like product was filtered off with suction and extracted by stirring 3 times with 150 ml of hexane each time and twice with 200 ml of methanol each time. After filtration with suction and drying in a vacuum cabinet at 50° C., 83 g (45%) of product were obtained.

EXAMPLE 8

The experiment was carried out analogously to Example 6, with the proviso that instead of 15 g of the oxyethylated tallow fatty alcohol, 30 g of this substance were employed.

The yield was 120 g (=65%).

The grafted polyvinylene carbonate groups were hydrolyzed by the method described in Examples 2–4, under b).

I claim:

1. A process for the preparation of a polymer consisting substantially of a base polymer having units (II) or a mixture of units (I) and (II), said units (I) and (II) having the following structural formulas

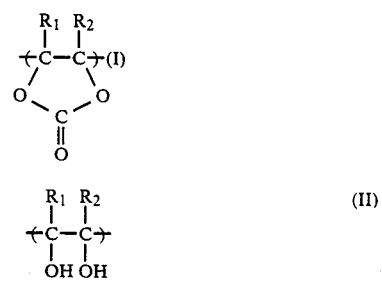

in which $R_1$ and $R_2$ are hydrogen or a monovalent hydrocarbon radical with up to 8 carbon atoms, which polymer also contains units which are derived from at least one compound of formula (III)

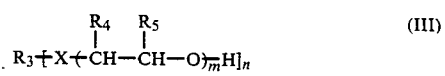

and grafted onto the base polymer in which:
$R_3$ is a hydrocarbon radical with 4 to 30 carbon atoms;
X is a member selected from the group consisting of —O—, COO— and mixture thereof;
$R_4$ and $R_5$ are hydrogen or a monovalent hydrocarbon radical with 1 to 8 carbon atoms, with the proviso that at least one of the radicals $R_4$ and $R_5$ is hydrogen;
m is an integer from 1 to 40; and n is an integer from 1 to 4,
which comprises polymerization of a compound of the formula (IV)

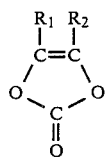

in which $R_1$ and $R_2$ are defined above, in the presence or absence of small amounts of other monomers copolymerizable with these compounds, the polymerization being carried out in a liquid dispersant in the presence of a free radical initiator, a dispersion stabilizer, and in the presence of at least one compound of the formula (III), in which $R_3$, $R_4$, $R_5$, X, m and n are as defined above, and using as the dispersion stabilizer a copolymer of maleic anhydride and at least one component selected from the group consisting of a vinyl alkyl ether, a vinyl ester and a longer-chain alpha-olefin to obtain a graft polymerization product per se or subjecting said product to hydrolysis of the cyclic carbonate groups.

2. A process as claimed in claim 1, wherein the dispersion stabilizer employed is a copolymer of maleic anhydride and at least one compound selected from the group consisting of a vinyl alkyl ether with 6 to 30 carbon atoms in the alkyl radical, a vinyl ester with 6 to 30 carbon atoms in the acyl group, and a longer-chain alpha-olefin with 8 to 30 carbon atoms.

3. A process as claimed in claim 1, wherein the dispersion stabilizer contains maleic anhydride and the comonomers in a ratio of about 1:1, wherein the dispersion stabilizer is used in an amount of 0.001 to 10% by weight based on the total amount of monomers, and wherein the vinyl alkyl ether is vinyl stearyl ether and the longer-chain alpha-olefin is octadec-1-ene.

4. A process as claimed in claim 1, wherein an oxyethylated alcohol, oxyethylated carboxylic acid, or a mixture of both, in an amount of 1 to 30% by weight based on the total amount of monomers, are employed as the compounds of the formula (III), and wherein the alcohol is a monohydric primary alcohol, the carboxylic acid is a monobasic primary carboxylic acid, and the hydrocarbon radical in both cases is an alkyl radical with 4 to 30 carbon atoms.

5. A process as claimed in claim 1, wherein a hydrocarbon with 6 to 20 carbon atoms or a light liquid paraffin is employed as the liquid dispersant.

6. A process as claimed in claim 1, wherein more than 50% of the cyclic carbonate groups of (I), based on the said amount of compounds (I) and (II), are converted into hydroxyl groups.

7. A process as claimed in claim 1, wherein at least 95% by weight of the cyclic carbonate groups are converted.

* * * * *